United States Patent [19]

Kollmeier et al.

[11] Patent Number: 4,609,750
[45] Date of Patent: Sep. 2, 1986

[54] SILOXANES WITH BETAINE GROUPS, THEIR SYNTHESIS AND USE IN HAIR CARE PRODUCTS

[75] Inventors: Hans-Joachim Kollmeier, Essen; Rolf-Dieter Langenhagen, Hattingen-Niederwenigern; Klaus Hoffmann, Essen, all of Fed. Rep. of Germany

[73] Assignee: Th. Goldschmidt AG, Essen, Fed. Rep. of Germany

[21] Appl. No.: 744,469

[22] Filed: Jun. 13, 1985

[30] Foreign Application Priority Data

Jun. 15, 1984 [DE] Fed. Rep. of Germany ....... 3422268

[51] Int. Cl.$^4$ .................................................. C07F 7/10
[52] U.S. Cl. .................................... 556/419; 424/70; 424/71; 252/117; 252/544; 252/547; 514/63
[58] Field of Search ............... 556/419; 424/70, 71; 252/117, 544, 547; 514/63

[56] References Cited

U.S. PATENT DOCUMENTS

| | | | |
|---|---|---|---|
| 4,104,296 | 8/1978 | Pike | 556/419 |
| 4,384,130 | 5/1983 | Martin | 556/419 X |
| 4,511,727 | 4/1985 | Martin | 556/419 X |

*Primary Examiner*—Paul F. Shaver
*Attorney, Agent, or Firm*—Toren, McGeady, Stanger, Goldberg & Kiel

[57] ABSTRACT

Organopolysiloxanes that have betaine groups and the following general formula

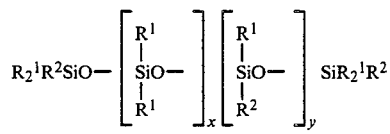

in which
$R^1$ can represent the same or different groups in the molecule and may be an alkyl radical with 1 to 18 carbon atoms, an aryl radical or a polyoxyalkylene radical with the proviso that at least 70% of the $R^1$ radicals are methyl radicals,
$R^2$ may be the same as $R^1$, with the proviso that at least one $R^2$ radical represents

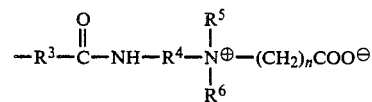

in which
$R^3$ is a divalent alkylene radical with 2 to 12 carbon atoms,
$R^4$ is a divalent alkylene radical with 2 to 6 carbon atoms,
$R^5$ and $R^6$ are the same or different and represent an alkyl radical with 1 to 4 carbon atoms or a benzyl radical, and
n = 1, 2, or 3,
x has a value of 0 to 200, and
y has a value of 1 to 50, as well as processes for their synthesis and their use in cosmetic preparations, especially in hair care products.

21 Claims, No Drawings

SILOXANES WITH BETAINE GROUPS, THEIR SYNTHESIS AND USE IN HAIR CARE PRODUCTS

BACKGROUND OF THE INVENTION

1. Field of the Invention

The invention relates to novel organopolysiloxanes with betaine groups and to processes for the synthesis of these compounds. It also relates to the use of these compounds in cosmetic preparations, especially in hair care products.

2. Description of the Prior Art

The use of organopolysiloxanes for the preparation of hair care products is well known. However, in "Chemie und Technologie der Silicone" (Chemistry and Technology of the Silicones) by Water Noll, Chemie Publishing House, 2nd edition, 1968, page 536, it is stated that normal polydimethylsiloxanols are unable to maintain the hairdo independently of the effects of moisture. Rather, the silicone would have to be fixed on the hair with the help of functional groups.

German Auslegeschrift 14 93 384 discloses organosiloxane compounds or mixtures of compounds having the formula:

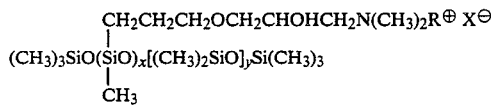

in which R represents hydrogen or $CH_3$, X represents halogen, x=1 to 10, and y=0 to 8.5, and the ratio of y:x is not greater than 8.5:1.

These organosiloxanes with quaternary ammonium groups can be synthesized by reacting an epoxysiloxane compound having the formula

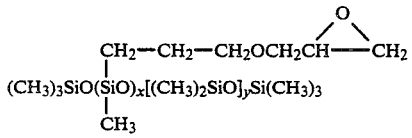

in a known manner with dimethylamine to obtain dimethylamino organosiloxane compound which having the formula

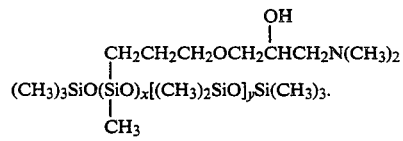

This compound is converted in a known manner with a hydrogen halide or with a methyl halide into the quaternary ammonium compound of the aforementioned formula.

According to U.S. Pat. No. 4,185,087, the aforementioned organopolysiloxanes with quaternary ammonium groups can be used for hair care products. As disclosed therein, simple aqueous shampoos may release soil from hair and remove an excess of grease. With most shampoos, however, degreasing of the hair would be carried out so thoroughly that damage to the hair could be observed. After washing, the hair becomes electrostatically charged and therefore difficult to comb. While the addition of lanolin derivatives, glycol, fatty esters or proteins improves the ability to handle the hair after washing, it does interfere with foaming. The hair would become somewhat sticky and feel unnatural. According to U.S. Pat. No. 4,185,087, the specified organopolysiloxanes with the quaternary ammonium groups should eliminate these disadvantages and improve the combability of the washed hair, give better hold to the hair set, and improve the gloss.

Similar teachings are contained in European Pat. Nos. 0 017 121 and 0 017 122 which describe organopolysiloxanes with quaternary ammonium groups for use in shampoos and hair conditioners to improve the combing properties of the hair. The compounds correspond to the general formula:

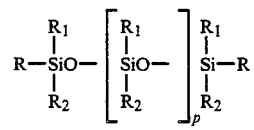

in which $R_1$ and $R_2$ represent an alkyl radical with 1 to 4 carbon atoms or an aryl radical, p represents the numbers 0 to 50, and R the radicals:

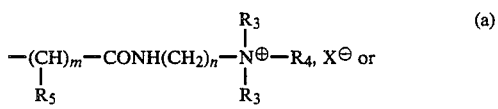

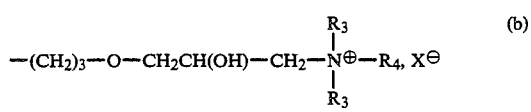

In formulas (a) and (b), $R_3$ represents an alkyl or hydroxyalkyl radical with 1 to 3 carbon atoms, $R_4$ represents a radical identical with $R_3$, aryl-$CH_2$-, or the allyl radical, $R_5$ represents hydrogen or the methyl radical, $X^{\ominus}$ represents the anions $Cl^{\ominus}$, $Br^{\ominus}$, $I^{\ominus}$, $CH_3SO_4^{\ominus}$ or $C_2H_5SO_4^{\ominus}$ and m the numbers 2 to 10 and n the numbers 2 to 4.

Finally, published European Patent Application 0 095 238 discloses a composition which essentially comprises the following components:

(A) a siloxane of the general formula

in which R is only described functionally as a group which brings about adhesion to the hair, for example, an amino, carboxyl or quaternary ammonium group, X is a hydrogen radical or a phenyl, hydroxyl or saturated hydrocarbon group with 1 to 8 carbon atoms, a has a value of 0 to 3, b has a value of 0 to 1 and n +m has a value of 1 to 1999, n having a value from 0 to 2000 and m a value of 1 to 2000;

(B) a surfactant;

(C) an additive for improving the freeze/thaw stability, and (D) water.

It therefore follows from the state of the art that organopolysiloxanes with quaternary ammonium groups have a strong substantivity on hair and endow it with good combability and gloss. However, their poor compatibility with anionic components, especially with anionic surfactants, is a disadvantage in hair care preparations. Moreover, they may also lead to irritation of the skin, especially of the mucous membrane, and to irritation of the eye which is extremely undesirable, especially in shampoos.

SUMMARY OF THE INVENTION

We have discovered novel siloxane derivatives for use as additives for hair cosmetics which have the desirable properties of the organopolysiloxanes with quaternary ammonium groups, but are compatible with anionic additives, especially with anionic surfactants. At the same time, the inventive siloxane derivatives are less irritating to the skin than prior art compounds.

More particularly, we have discovered that organopolysiloxanes, which have one or more betaine groups, exhibit these properties. The compounds of the present invention have the general formula

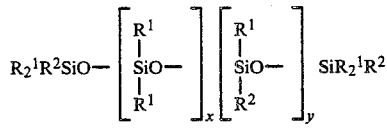

I in which $R^1$ can represent the same or different groups in the molecule and may be an alkyl radical with 1 to 18 carbon atoms, an aryl radical or a polyoxyalkylene radical with the proviso that at least 70% of the $R^1$ radicals are methyl radicals, $R^2$ may be the same as $R^1$, with the proviso that at least one $R^2$ radical represents the

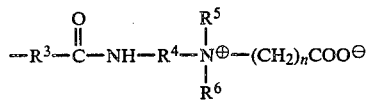

group,
in which
$R^3$ is a divalent alkylene radical with 2 to 12 carbon atoms,
$R^4$ is a divalent alkylene radical with 2 to 6 carbon atoms,
$R^5$ and $R^6$ are the same or different and represent an alkyl radical with 1 to 4 carbon atoms or a benzyl radical, and
n=1, 2, or 3,
x has a value of 0 to 200, and
y has a value of 1 to 50.

It is evident from the general formula I that the betaine group(s) may be linked terminally or laterally.

The present invention also comprises a method for the synthesis of the inventive organopolysiloxanes with betaine groups which comprises reacting in a known manner, compounds having the general formula

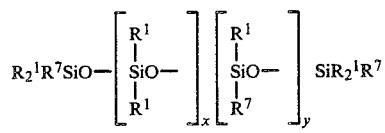

II in which $R^7$ may be the same as $R^1$ with the proviso that at least one of the $R^7$ radicals is the hydrogen radical, with equimolar amounts in respect to the SiH groups, with compounds having the general formula:

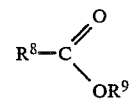

III in which
$R^8$ is an alkylene radical with a terminal double bond and 2 to 12 carbon atoms or a cycloalkylene radical with 6 to 12 carbon atoms, and
$R^9$ is a hydrogen or alkyl radical with 1 to 4 carbon atoms, in the presence of platinum or palladium catalysts. The product obtained is then reacted in a known manner with compounds having the general formula:

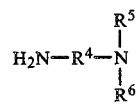

IV and the product obtained is finally quaternized in a known manner with equimolar amounts of compounds having the general formula:

X—(CH$_2$)$_n$COOY    V in which
X is a chlorine or bromine radical, and
Y is an alkali radical.

DESCRIPTION OF THE PREFERRED EMBODIMENTS

At least 70% of the $R^1$ radicals are methyl radicals. Especially preferred are those polysiloxanes in which all the $R^1$ radicals are methyl radicals. Up to 30% of the $R^1$ radicals may be alkyl radicals, with 2 or more and, preferably, with 12 to 18 carbon atoms, or aryl radicals. Examples of such alkyl radicals are the ethyl, propyl, isopropyl, butyl, hexyl, isooctyl, decyl, dodecyl hexadecyl or stearyl radicals. The aryl radical generally is a phenyl radical. The alkyl radicals as well as the aryl radicals may be substituted.

It is also possible that up to 30% of the $R^1$ radicals are polyoxyalkylene radicals and especially those having the general formula:

—(CH$_2$)$_3$O(C$_m$H$_{2m}$O)$_p$Q in which the —(C$_m$H$_{2m}$O)$_p$ group is built up from ethylene oxide and propylene oxide and m has an average value of 2.0 to 2.6, p has a value of 1 to 25, and Q is a hydrogen or alkyl radical with 1 to 4 carbon atoms. Compounds are preferred in which 3 to 10% of the $R^1$ radicals are polyoxyalkylene radicals.

At least one $R^2$ radical must represent the

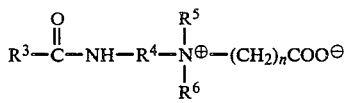

group. $R^3$ and $R^4$ are in each case bivalent alkylene radicals. $R^3$ can have up to 12, and $R^4$ up to 6 carbon atoms. Preferably, $R^3$ is an alkylene radical with 2 to 10 carbon atoms and $R^4$ an alkylene radical with 2 to 4 carbon atoms. In this connection, $R^5$ and $R^6$ preferably are methyl radicals. They may, however, also be ethyl, propyl, or butyl radicals or a benzyl radical. In this formula, n has a value of 1, 2, or 3; n =1 being preferred.

The value of x preferably is 2 to 100 and especially 5 to 50, while the value of y is 1 to 25 and especially 2 to 10.

Examples of inventive organopolysiloxanes with betaine groups are:

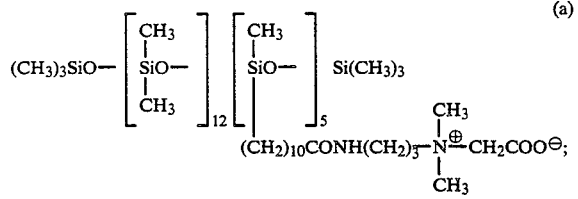

(a)

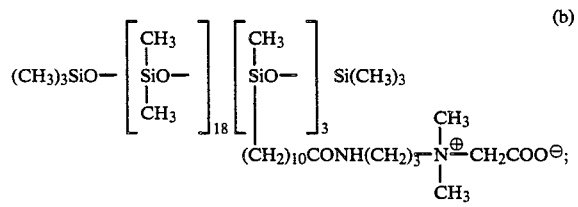

(b)

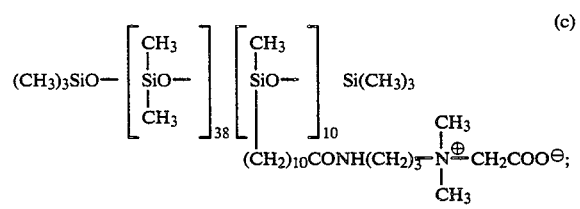

(c)

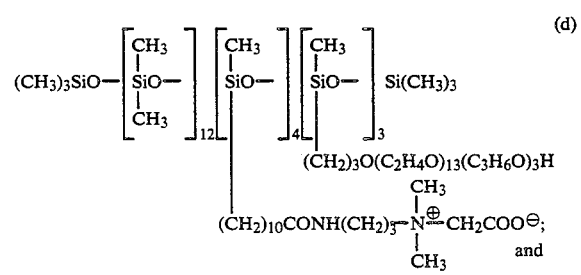

(d)

and

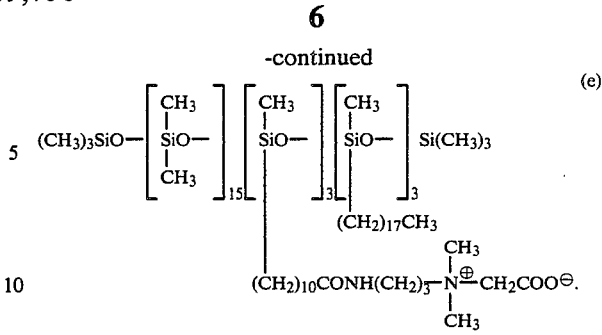

(e)

The inventive compounds generally are viscous to highly viscous, oily to pasty, and colorless to yellow products. The solubility of the inventive compounds is essentially determined by the ratio of the number of betaine groups to the number of siloxy units ($R_2^1SiO$) as well as by the nature of the $R_1$ radicals. Higher betaine group contents and/or the presence of polyoxyalkylene radicals with a predominant proportion of oxyethylene units result in products, which are soluble in water and lower alcohols or glycols. On the other hand, oil compatible or oil dispersible products can be obtained by incorporating alkyl radicals with 12 to 18 carbon atoms. Products which are soluble in water or glycols, are generally preferred for use in hair care products.

In the process of the invention, platinum or palladium compounds are used to catalyze the addition of compounds III, which contain an olefinic double bond, to hydrogensiloxanes II. A suitable catalyst is $H_2PtCl_6.6H_2O$. Other particularly suitable catalysts are known from German Pat. No. 31 33 869. They are employed in amounts of $10^{-2}$ to $10^{-8}$ moles per mole of SiH groups in the siloxane. Preferred addition temperatures are 40° to 160° C. and especially 50° to 120° C. If an inert solvent is used, the boiling point of this solvent determines the upper temperature limit.

The reaction product obtained from the addition reaction is converted by reaction with compounds IV into the acid amide and finally quaternized with compounds V. These reactions also proceed in a known manner, preferably at temperatures from 40° to 160° C. As inert solvents, alcohols, glycols, or water may be used. The end product can then be freed from the alkali salt by filtration.

The inventive compounds exhibit the desired combination of properties. They are compared in the following Table with similar products used according to the state of the art.

TABLE

| Additive | Substantivity on Hair | Combability and Gloss of Hair | Skin Irritation | Compatibility with Anionic Additives |
|---|---|---|---|---|
| Siloxane with polyether groups | weak | weak | none | good |
| Siloxane with anionic groups | none | none | weak | good |
| Siloxane with amino groups | average | average | average | good |
| Siloxane with quaternary amino groups | strong | good | weak | poor |
| Siloxane with betaine groups | average | good | none | good |

TABLE-continued

| Additive | Substantivity on Hair | Combability and Gloss of Hair | Skin Irritation | Compatibility with Anionic Additives |
|---|---|---|---|---|
| Siloxane-free betaine | average | none | none | good |

It can be seen from the Table that the organopolysiloxanes with betaine groups have the desired combination of properties, which is not exhibited by any of the other compounds.

It is therefore a further object of the invention to use the inventive compounds in cosmetic preparations, especially in preparations for the care of hair. In this connection, hair cosmetics can be shampoos or hair conditioner, depending on whether the emphasis is on the cleansing effect or on the care effect and the effect of better combability. Shampoos to which the inventive organopolysiloxane with betaine groups have been added in amounts of 0.1 to 10 weight percent, and which contain up to 30 weight percent of substances with detergent activity, besides water and possibly other additives, cause the washed hair to have fullness and an agreeable handle, to show the desired gloss and to be easily combable. Practically no electrostatic charging of the hair is observed. In hair care products, such as, hair tonics or hair sprays, the inventive compounds in amounts of 0.1 to 5% already bring about a significant improvement in combability of the hair and development of fullness and gloss.

Conventional additives, such as, solvents, thickeners, perfumes, preservatives, complexing agents, foam stabilizers, opacifiers, luster developing agents or other conventional additives, such as, dyes, may be added to the hair care products.

The following are examples of recommended formulations for hair care products:

| Material for a Cream-Treatment Rinse | |
|---|---|
| Cetyl alcohol | 6 parts by weight |
| TEGINACID ® H* | 6 parts by weight |
| Glycerin | 3 parts by weight |
| Betaine siloxane (Example 1) | 2 part by weight |
| Water | 83 parts by weight |
| Conditioning Shampoo | |
| (a) Sodium lauryl ether sulfate | 3 parts by weight |
| Ammonium alkyl ether sulfate | 6 parts by weight |
| TAGAT ® KL 141* | 5 parts by weight |
| Betaine siloxane (Example 1) | 2 parts by weight |
| Water | 84 parts by weight |
| (b) Coconut fatty acid diethanolamide | 0.5 parts by weight |
| Sodium lauryl ether sulfate | 30 parts by weight |
| Salt | 1.5 parts by weight |
| TEGO ® -Betaine L 7* (alkylamidobetaine), | 8 parts by weight |
| Betaine siloxane (Example 1) | 2 parts by weight |
| Water | 58 parts by weight. |

*TEGINACID is a registered trademark of Th. Goldschmidt AG. Under the product name TEGINACID H, a mixture of glycerin mono- and distearate with a small proportion of polyglycol fatty alcohol ethers is sold.
*TAGAT is a registered trademark of Th. Goldschmidt AG. Under the product name TAGAT KL 141, polyoxyethylene propylene glycol dioleate is sold.
*TEGO is a registered trademark of Th. Goldschmidt AG. Under the product name TEGO-Betain L 7, a cocamido propyl betaine (1-alkylamino-3-dimethylammonium-propane-3-carboxymethylbetaine) is sold.

The inventive compounds may also be added to skin care products. As a component of soap or skin creams, they form a fine, non-irritating, non-greasy film on the skin. In contrast to dimethylsiloxanes of low viscosity, especially the cyclic dimethylsiloxanes, they do not evaporate on the skin and therefore provide constant protection.

A liquid soap may have the following composition:

| | |
|---|---|
| TAGAT ® 0 2* | 1 part by weight |
| Coconut fatty acid diethanolamide | 0.5 parts by weight |
| Sodium lauryl ether sulfate | 30 parts by weight |
| TEGO ® -betaine L 7* (alkylamidobetaine), | 7 parts by weight |
| Salt | 2 parts by weight |
| Betaine siloxane (Example 3) | 3 parts by weight |
| Water | 56.5 parts by weight |

*TAGAT is a registered trademark of Th. Goldschmidt AG. Under the product name TAGAT 0 2, a polyoxyethylene glycerin monooleate is sold.

The inventive process is explained in greater detail in the following examples. Furthermore, application-related tests are shown for comparison with products of the state of the art.

EXAMPLE 1

Synthesis of the siloxane, containing betaine groups and having the following formula:

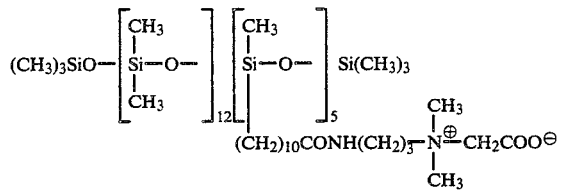

(a) First, 123.9 g of methyl undecylenate and 0.15 g of a 10% solution of $H_2PtCl_6.6\ H_2O$ in i-propanol is added to a flask, equipped with stirrer, thermometer, gas inlet and reflux condenser. This mixture is heated to 120° C. and 169.1 g of a siloxane, the average formula of which is represented by:

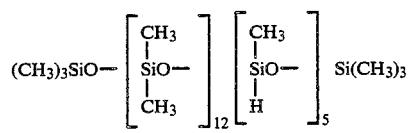

are added dropwise over a period of 20 minutes. The reaction is carried out under a blanket of nitrogen. After 4.5 hours, analysis of the active hydrogen still present shows that there has been a conversion of 92%. The mixture is treated with 5 g of sodium bicarbonate, stirred for 30 minutes and filtered, 280 g of a siloxane, the average formula of which is represented by

A

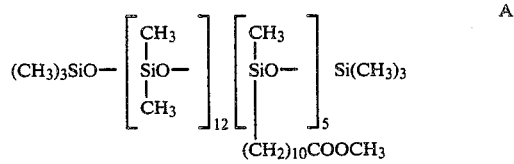

being obtained.

(b) In a flask, equipped with stirrer, thermometer, gas inlet and facilities for distillation, 234.5 g (=0.1 mole) of the siloxane A obtained and 100 g of 3-dimethylamino-1-propylamine (corresponding approximately to a 100% excess) are mixed. While a slow stream of nitrogen is being passed in, the mixture is heated to 130° C. and stirred for 1 hour. The temperature is then increased to 160° C. and kept there for 2 hours. At the same time, 17.5 g of distillate are obtained. The mixture is cooled and the excess amine is removed by distillation at a bath temperature of 140° C. under a vacuum produced by a water jet. A yellow-brown, clear, viscous liquid is obtained as residue. Analysis reveals an amine nitrogen content of 2.55% (theoretical: 2.60%). The siloxane obtained corresponds to the average formula

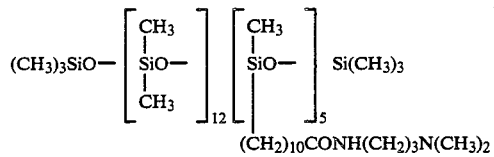

B (c) In a flask equipped with stirrer, thermometer and reflux condenser, 164.8 g (=0.3 moles amino groups) of the siloxane of Formula B and 34.9 g (=0.3 moles) ClCH2COONa in 150 g of water and 50 g of isopropanol are stirred for 5 hours at 85° C. After about 1 hour, the mixture becomes clear. When the reaction is completed, 2.6% ionic chlorine can be determined in the solution obtained; this corresponds to a conversion of 97.7%. The solvent is subsequently distilled off up to a bath temperature of 70° C. in a rotary evaporator under the vacuum of a water jet. A cloudy residue remains, which is almost solid at room temperature. In order to remove the sodium chloride formed, the residue is taken up in i-propanol and filtered. The solution is subsequently concentrated once again in a rotary evaporator. A clear, light brown product is obtained, which is barely free-flowing at room temperature. Analysis reveals a betaine-group nitrogen content of 2.0% (theoretical: 2.31%).

EXAMPLE 2

Synthesis of the siloxane, containing betaine groups and having the following formula:

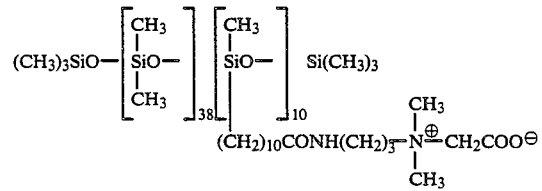

(a) First, as in step (a) of Example 1, methyl undecylenate is added to a siloxane having the formula

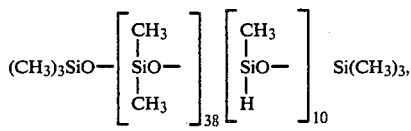

to obtain a siloxane having the formula

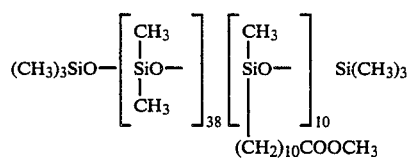

C (b) The siloxane of formula C (278.2 g=0.05 moles) is reacted as described in step (b) of Example 1, with 100 g (corresponding to about a 100% excess) of 3-dimethyamino-1-propylamine. During the reaction, 15.5 g of distillate result. The product obtained is a yellow-brown, clear viscous liquid and contains 2.2% amine nitrogen (theoretical: 2.24%). The product corresponds to the formula

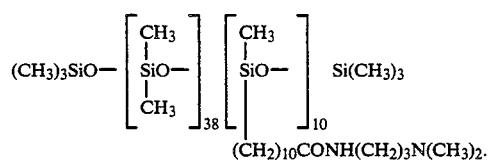

D (c) In a flask provided with stirrer, thermometer and reflux condenser, 254.7 g (=0.4 moles amino groups) of the siloxane of formula D, a solution of 46.6 g (=0.4 moles) of ClCH2COONa in 254.5 g of water, as well as 370.5 g of 1,2-propylene glycol are mixed and stirred for 5 hours at 100° C. The mixture becomes clear after about 1 hour. After the reaction, 1.45% ionically bound chlorine can be determined in the clear, yellow solution obtained. This corresponds to a conversion of 94.8%. The content of nitrogen, bound to the betaine in the solution, is 0.56% (theoretical: 0.60%).

The solution obtained contains 30 weight percent of the inventive siloxane, 2.5 weight percent of sodium chloride, 27.5 weight percent of water and 40 weight percent of 1,2-propylene glycol.

EXAMPLE 3

Synthesis of the siloxane, containing betaine groups and having the following formula

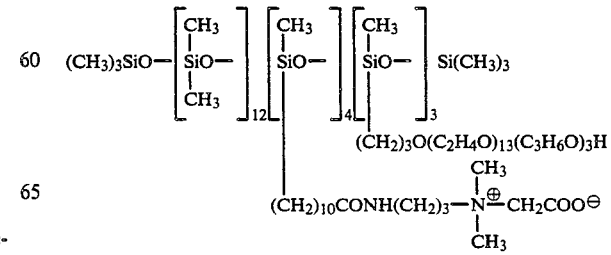

(a) First, a mixture of 99.2 g of methyl undecylenate, 301.5 g of a polyoxyalkylene monool having the formula

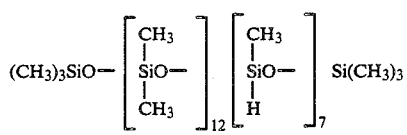

and 0.3 g of a 10% solution of $H_2PtCl_6 \cdot 6H_2O$ in i-propanol are reacted, as described in step (a) of Example 1, with 184.1 g of a siloxane of the average formula The conversion amounts to 89.5%. A siloxane having the average formula

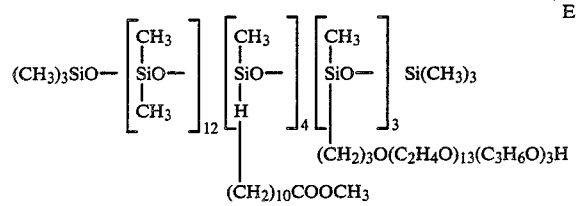

in an amount of 564 g is obtained.

(b) As in step (b) of Example 1, 467.8 g (=0.1 moles) of the siloxane of formula E are reacted with 82 g (corresponding to an excess of about 100%) of 3-dimethylamino-1-propylamine. In so doing, 12 g of distillate result. The siloxane obtained is a yellow-brown, clear, viscous liquid. The amine nitrogen content is 1.08% (theoretical: 1.13%). The siloxane corresponds to the formula

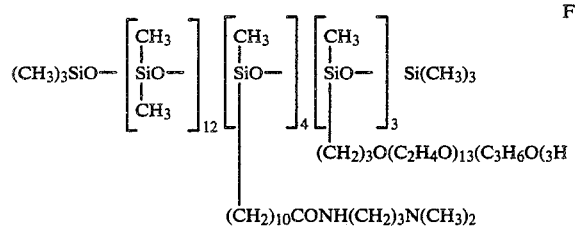

(c) In a flask equipped with stirrer, thermometer and reflux condenser, 259.4 g (=0.2 moles of amino groups) of the siloxane of formula F and a solution of 23.3 g (=0.2 moles) of $ClCH_2COONa$ in 259.3 g of water, as well as 135.5 g of 1,3-propylene glycol are mixed and stirred for 5 hours at 100° C. The mixture becomes clear after about one half hour. After the reaction, 1.0% of ionically linked chlorine can be determined in the clear, yellow solution; this amount corresponds to a conversion of 95.2%. The amount of betaine-linked nitrogen in the solution is 0.38% (theoretical: 0.41%).

The solution obtained contains 40 weight percent of the inventive siloxane, 1.7 weight percent of sodium chloride, 38.3 weight percent of water and 20 weight percent of 1,2-propylene glycol.

EXAMPLE 4

Testing the Inventive Compounds in Hair Care Products A conditioning shampoo of the following composition:

| | |
|---|---|
| Sodium laurylether sulfate | 3 parts by weight |
| Ammonium alkylether sulfate | 6 parts by weight |
| TAGAT ® KL 141* | 5 parts by weight |
| Betaine siloxane (Example 2) | 2 parts by weight |
| Water | 83 parts by weight |

*TAGAT is a registered trademark of Th.Goldschmidt AG. Under the product name, TAGAT KL 141, a polyoxyethylene propylene glycol dioleate is sold.

is compared in respect to its action with a shampoo formulation in which the inventive betaine siloxane is replaced by a cationic organosiloxane compound as described in German Auslegeschrift legeschrift 14 93 384, wherein x=15, y=5 and $X=Cl^\ominus$.

The preparation with the betaine siloxane is clear, while the cationic siloxane leads to cloudiness.

The half-side comparison of the practical application on human hair resulted in the following evaluation:

With respect to foaming, the creaminess of the foam, the dry combability, the anti-electrostatic effect and the fullness of the hair, the inventive betaine siloxane is superior. The cationic siloxane gives a somewhat better result only with respect to the wet combability. This is, however, associated with a heavier loading and therefore a lesser fullness of the hair.

We claim:

1. Compounds having the formula

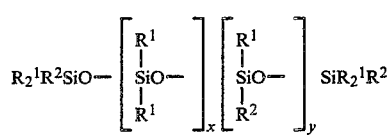

in which
$R^1$ can represent the same or different groups in the molecule and may be an alkyl radical with 1 to 18 carbon atoms, an aryl radical or a polyoxyalkylene radical with the proviso that at least 70% of the $R^1$ radicals are methyl radicals, $R^2$ may be the same as $R^1$, with the proviso that at least one $R^2$ radical represents

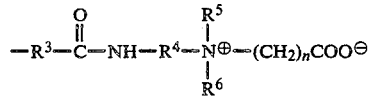

in which
$R^3$ is a divalent alkylene radical with 2 to 12 carbon atoms,
$R^4$ is a divalent alkylene radical with 2 to 6 carbon atoms,
$R^5$ and $R^6$ are the same or different and represent an alkyl radical with 1 to 4 carbon atoms or a benzyl radical, and
n=1, 2, or 3,
x has a value of 0 to 200, and
y has a value of 1 to 50.

2. The compound of claim 1 wherein up to 30% of the $R^1$ radicals are alkyl and have 2 or more carbon atoms.

3. The compound of claim 1 wherein up to 30% of the $R^1$ radicals are alkyl and have from 12 to 18 carbon atoms.

4. The compound of claim 1 wherein up to 30% of the $R^1$ radicals are alkyl and are selected from the group consisting of ethyl, propyl, isopropyl, butyl, hexyl, isooctyl, decyl, dodecyl hexadecyl and stearyl.

5. The compound of claim 1 wherein up to 30% of the $R^1$ radicals are phenyl.

6. The compound of claim 1 wherein up to 30% of the $R^1$ radicals are polyoxyalkylene radicals having the formula $$-(CH_2)_3O(C_mH_{2m}O)_pQ$$

in which the $-(C_mH_{2m}O)_p$ group is built up from ethylene oxide and propylene oxide and m has an average value of 2.0 to 2.6, p has a value of 1 to 25, and Q is a hydrogen or alkyl radical with 1 to 4 carbon atoms.

7. The compound of claim 6 wherein from 3 to 10% of the $R^1$ radicals are polyoxyalkylene.

8. The compound of claim 1 wherein $R^3$ contains from 2 to 10 carbon atoms and $R^4$ contains 2 to 4 carbon atoms.

9. The compound of claim 1 wherein $R^5$ and $R^6$ are selected from the group consisting of methyl, ethyl, propyl, butyl and benzyl.

10. The compound of claim 8 wherein $R^5$ and $R^6$ are selected from the group consisting of methyl, ethyl, propyl, butyl and benzyl.

11. The compound of claim 1 wherein x is 2 to 100 and y is 1 to 25.

12. The compound of claim 11 wherein x is 5 to 50 and y is 2 to 10.

13. A compound selected from the group consisting of

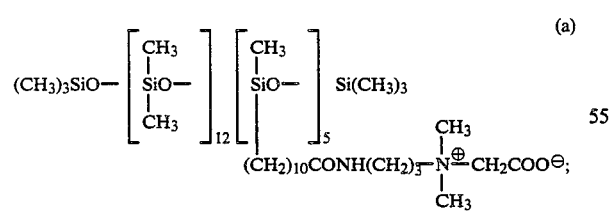
(a)

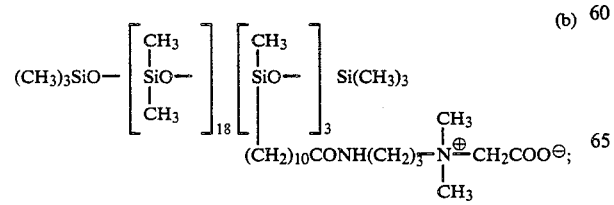
(b)

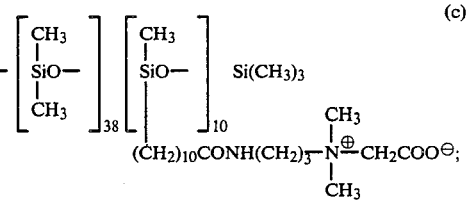
(c)

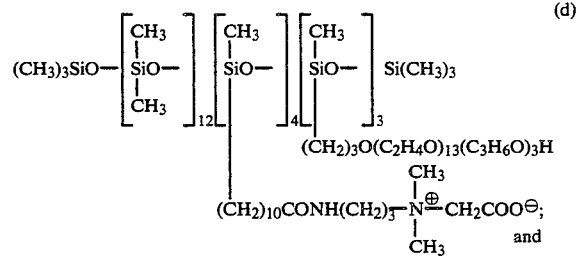
(d)

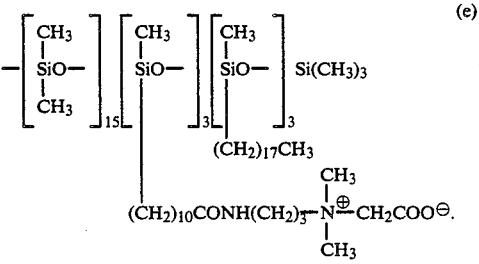
(e)

14. a process for the synthesis of the compounds of claim 1 comprising reacting, in a known manner, compounds having the formula

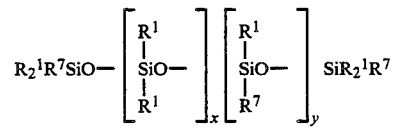

in which $R^7$ may be the same as $R^1$ with the proviso that at least one of the $R^7$ radicals is the hydrogen radical, with equimolar amounts in respect to the SiH groups, with compounds having the formula:

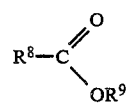

in which $R^8$ is an alkylene radical with a terminal double bond and 2 to 12 carbon atoms, or a cycloalkylene radical with 6 to 12 carbon atoms, and $R^9$ is a hydrogen or alkyl radical with 1 to 4 carbon atoms, in the presence of platinum or palladium catalysts; and reacting the product obtained in a known manner, with compounds having the formula:

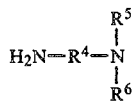

and quaternizing the product obtained in a known manner with equimolar amounts of compounds having the formula:

X—(CH$_2$)$_n$COOY in which
X is a chlorine or bromine radical, and
Y is an alkali radical.

15. The process of claim 14 wherein the catalyst is H$_2$PtCl$_6$.6H$_2$O.

16. The process of claim 14 wherein the catalyst is used in an amount from $10^{-2}$ to $10^{-8}$ moles of SiH groups in the siloxane.

17. The process of claim 14 wherein the reaction of compounds II and III is carried out at a temperature from 40° to 160° C.

18. The process of claim 14 wherein the reaction of compounds II and III is carried out at a temperature from 50° to 120° C.

19. The process of claim 14 wherein the reaction of compounds II and III is carried out in an inert solvent at a temperature from 40° C. to the boiling point of the solvent.

20. The process of claim 14 wherein the solvent for the final quaternizing reaction is an alcohol, glycol or water.

21. A cosmetic preparation containing a cosmentic effective amount of the compound of claim 1, said cosmetic preparation being selected from the group consisting of soaps, shampoos, hair conditioners, and skin conditioners.

* * * * *